United States Patent
Al Hosani et al.

(10) Patent No.: US 10,422,754 B2
(45) Date of Patent: Sep. 24, 2019

(54) ONLINE MEASUREMENT OF BLACK POWDER IN GAS AND OIL PIPELINES

(71) Applicant: The Petroleum Institute, Abu Dhabi (AE)

(72) Inventors: Esra Al Hosani, Abu Dhabi (AE); Mahmoud Meribout, Abu Dhabi (AE)

(73) Assignee: Khalifa University of Science and Technology, Abu Dhabi (AE)

(*) Notice: Subject to any disclaimer, the term of this patent is extended or adjusted under 35 U.S.C. 154(b) by 0 days.

(21) Appl. No.: 14/639,473

(22) Filed: Mar. 5, 2015

(65) Prior Publication Data
US 2016/0258876 A1  Sep. 8, 2016

(51) Int. Cl.
| | | |
|---|---|---|
| G01N 21/85 | (2006.01) | |
| G01J 3/42 | (2006.01) | |
| G01J 3/44 | (2006.01) | |
| G01J 3/02 | (2006.01) | |
| G01J 3/28 | (2006.01) | |

(52) U.S. Cl.
CPC ............ *G01N 21/85* (2013.01); *G01J 3/0218* (2013.01); *G01J 3/0264* (2013.01); *G01J 3/0278* (2013.01); *G01J 3/2803* (2013.01); *G01J 3/42* (2013.01); *G01J 3/44* (2013.01); *G01J 3/4412* (2013.01); *G01N 2021/8578* (2013.01)

(58) Field of Classification Search
CPC .. G01N 21/8507; G01N 21/359; G01N 21/94; G01N 21/65; G01N 21/85
See application file for complete search history.

(56) References Cited

U.S. PATENT DOCUMENTS

| | | | |
|---|---|---|---|
| 5,140,169 A | 8/1992 | Evens et al. | |
| 5,170,056 A | 12/1992 | Berard et al. | |
| 5,418,614 A | 5/1995 | Brost et al. | |
| 5,742,064 A | 4/1998 | Infante | |
| 5,781,284 A * | 7/1998 | Infante ................... | G01N 21/85 356/432 |
| 8,379,205 B2 | 2/2013 | Palmskog et al. | |
| 8,686,364 B1 | 4/2014 | Little et al. | |

(Continued)

FOREIGN PATENT DOCUMENTS

| | | |
|---|---|---|
| CN | 201355340 | 12/2009 |
| EP | 1061356 | 12/2000 |
| WO | 200902322 A1 | 12/2008 |

OTHER PUBLICATIONS

E. Al Hosani, "A New Non Destructive Device for Real-Time Measurement of Black Powder Particles in Gas Pipelines," Thesis, The Petroleum Institute, Sep. 2012.

(Continued)

*Primary Examiner* — Maurice C Smith
(74) *Attorney, Agent, or Firm* — 24IP Law Group USA, PLLC; Timothy R. DeWitt

(57) ABSTRACT

A method and system for determination of contaminants, such as black powder, in a flowing fluid, such as natural gas, is disclosed. The method comprises transmitting a plurality of light beams over a spectrum of wavelengths through the flowing fluid and receiving a plurality of measurements relating to transmitted and scattered light beams over the spectrum of wavelengths. The received plurality of measurements are compared with a plurality of stored patterns and a result indicative of the determination of the contaminants is output.

14 Claims, 16 Drawing Sheets

(56) References Cited

U.S. PATENT DOCUMENTS

| | | | |
|---|---|---|---|
| 2004/0179194 A1* | 9/2004 | Schmilovitch | G01N 21/05 356/244 |
| 2010/0275677 A1* | 11/2010 | Gibbs | B05B 12/08 73/53.01 |
| 2013/0031964 A1 | 2/2013 | Tunheim et al. | |
| 2014/0060204 A1* | 3/2014 | Ahmed | G01F 1/56 73/861.04 |
| 2014/0085630 A1* | 3/2014 | Bell | G01J 3/28 356/301 |
| 2015/0021482 A1 | 1/2015 | Mueller et al. | |
| 2015/0279072 A1* | 10/2015 | Black | G06T 11/60 382/109 |

OTHER PUBLICATIONS

E. Al Hosani, M. Meribout, A. Al-Durra, K. Al-Wahedi and S. Teniou, "A New Optical-Based Device for Online Black Powder Detection in Gas Pipelines," IEEE Transactions on Instrumentation and Measurement, vol. 63, No. 9, Sep. 2014.

A. Sherik and B. Davis, "Thermodynamic Analysis of Formation of Black Powder in Sales Gas Pipelines," Saudi Aramco Journal of Technology Fall 2009, pp. 17-23.

O. Trifilieff and T. Wines, "Black Powder Removal from Transmission Pipelines: Diagnostics and Solutions," Pipeline Rehabilitation & Maintenance Conference, Gulf International Convention Center, Bahrain, Jan. 19-21, 2009.

Abou-Khousa Mohamed et al. "Hermetically Sealed Microwave Probe for in-situDetection of Black Powder in Gas Pipelines," Conference Record—IEEE Instrumentation and Measurement Technology Conference, pp. 1115-1119 (2014).

* cited by examiner

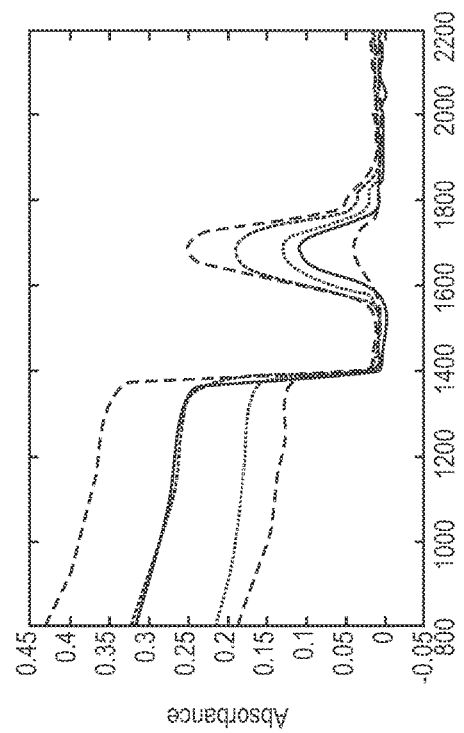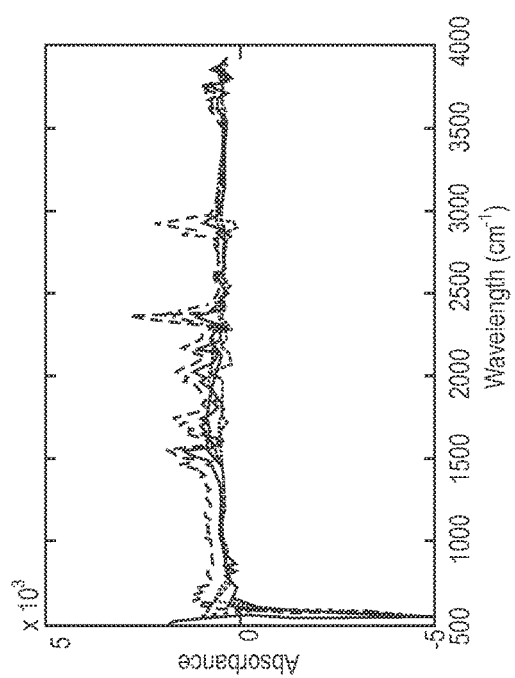

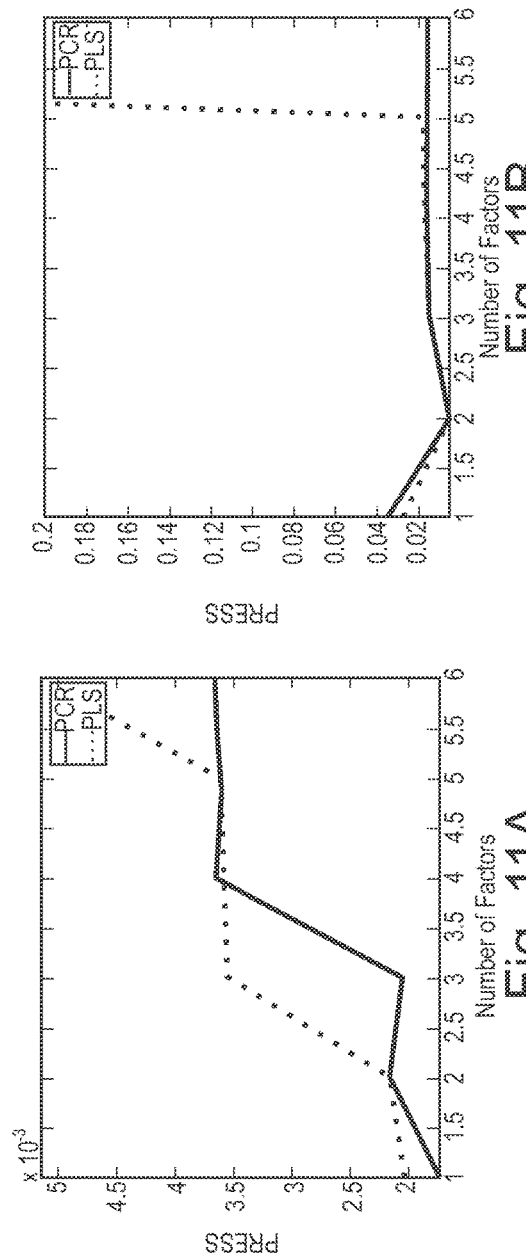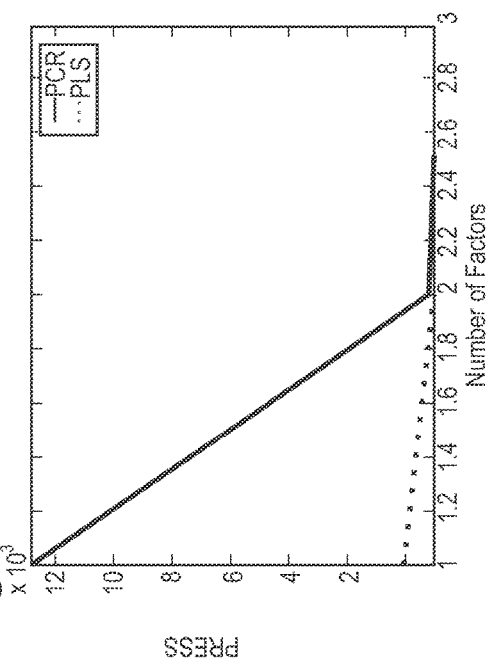
Fig. 11A
Fig. 11B
Fig. 11C

|  | MIR range | NIR range | | | Raman Range | |
|---|---|---|---|---|---|---|
|  | PLSR (2 factors) | PCR (3 factors) | PLSR (2 factors) | PCR (2 factors) | PLSR (2 factors) | PCR (2 factors) |
| PRESS | 0.002099 | 0.002126 | 0.005467 | 0.005344 | 0.0002329 | 0.0002402 |
| $R^2$ | 0.9753 | 0.9744 | 0.9744 | 0.9743 | 0.998199 | 0.998165 |
| MSPE | 0.0001983 | 0.0002068 | 0.0008731 | 0.0009065 | 5.04e-5 | 5.099e-5 |

Fig. 16

ONLINE MEASUREMENT OF BLACK POWDER IN GAS AND OIL PIPELINES

CROSS-REFERENCE TO RELATED APPLICATIONS

None.

STATEMENT REGARDING FEDERALLY SPONSORED RESEARCH OR DEVELOPMENT

None.

BACKGROUND OF THE INVENTION

Field of the Invention

This invention relates to a device that allows an online measurement of the concentration of contaminants, such as black powder, that may be generated and transported through a natural gas or oil pipeline.

Brief Description of the Related Art

"Black powder" is a general term used for solid contaminants, which can be found in a gas or fluid pipeline. The black powder occurs from various and many unknown reasons. In oil and gas fields, the black powder is known to comprise solid particles of micrometer size. It is composed of various molecular compositions that usually contain one of the derivations of iron oxide (e.g. $Fe_2O_3$ or $Fe_3O_4$) which originate from the internal walls of the steel-made pipelines. Other molecules such as sulfur dioxide ($SO_2$) may also be present due to the abundance of the hydrogen sulfide in oil and gas wells.

The black powder has numerous forms and may be wet and/or have a tar-like appearance. It typically comprises very fine particles (often sub micrometer in size) of iron sulfide, iron oxide, and iron carbonate (see Sherik and Davis "Thermodynamic analysis of formation of black powder in sales gas pipelines, Saudi Aramco J. Technol., Vol. 1, pp 17-23, March 2009). As these fine particles flow in the gas pipeline, the particles of the black power can accumulate around the control valves, compressors, and other equipment, which may create a severe pressure drop and in some cases lead to an entire shutdown of the pipeline and thus of the production. The problems may extend further to the utility companies connected to the actual network pipeline (e.g. electricity companies) in which their various pieces of equipment are damaged and electricity production declines.

These issues have led to gas production companies to implement measures for mitigating the propagation of black powder in their gas pipelines, as reported in Trifilieff et al "Black power removal from transmission pipelines: Diagnostics and solution", presented at the Pipeline Rehabilitation Maintenance Conference, Gulf Int. Convention Center, Manama, Bahrain, January 2009, pp 1-12. Despite all separation techniques applied currently to the gas pipelines to eliminate the black powder (e.g., filtering, cyclones, and pigging), the problem still exists. The difficulties in resolving the issue can be at least partly explained by the fact that the size of black powder particles are on the order of sub micrometers and are thus hard to extract from the flowing gas in the gas pipeline. Consequently, new strategies are being now investigated.

One approach is to monitor propagation of the black powder at different points of the pipeline network, which helps in taking more effective preventive actions against the buildup of the black powder. Currently, there is no existing system for inline measurement of the black powder, within either natural gas or petroleum continuous phases.

In other different industrial applications optical-based techniques such as NIR, MIR and Raman spectroscopy have been used for monitoring fluid conditions. These prior art methods usually comprise the scanning of the target fluid over a large range of wavelengths in either the transmission or reflection mode.

The following patents illustrate the use of such optical-based techniques.

U.S. Pat. No. 8,379,205 B2, issued February, 2013 suggests an arrangement for determining the concentration of substances in a fluid. The system comprises a light source and a light source splitter (consisting of fiber Bragg grating), which generates a relatively small number of secondary light beams (e.g. around three light beams) at different wavelengths. The secondary light beams impact the fluid in a time-multiplexed manner and a number of photosensitive detectors, corresponding to the number of light beams (e.g. around 3 detectors), generate a plurality of electrical signals that are proportional to the composition and the concentration of the substance in the measured fluid.

The apparatus of U.S. Pat. No. 8,379,205 B2 is not suitable for black powder detection in oil or gas pipelines for several reasons. The analysis of the light intensity of the transmitted light beams through the fluid for a relatively small number of wavelengths (in this case three) will not be effective because of the complex wavelength spectrum that is obtained for various concentrations of black powder, especially when present within different continuous phases.

U.S. Pat. No. 5,742,064 issued Apr. 21, 1998 suggests a method to determine the amount of dirt and water in oil when a target oil is passing through a given section of the pipeline. The apparatus of the '064 patent comprises a tunable laser light which emits coherent light towards the target oil. A photomultiplier or a spectrometer are present to sense the received light from the target oil. This received light is proportional to the amount of dirt and water existing in the target oil. The application addressed in this '064 patent is different from the teachings of the current disclosure. The algorithm disclosed in the '064 patent is based around a simple search for the best match of the spectrum of the received light within a database of existing spectra and may not be always effective due to the high complexity and sensitivity of the wavelength spectrum from the target oil. More complex algorithms (e.g. pattern recognition algorithms) are usually required in practice.

U.S. Pat. No. 5,418,614 issued May 23, 1995 suggests a method for online analysis of online fluids streams. The invention uses a general-purpose optical photometer in the ultraviolet, visible and near infrared spectral ranges. The light source generates light signals, which are carried via optical fiber cables between a central photometric console and remote analysis sites in which the captured signals are compared with a reference signal. Although the disclosure in this patent application shares some similarities with the current disclosure by using optical light (NIR), the teachings of the '614 patent differs from the current disclosure by the use of a photomultiplier in the detection process, instead of photodiodes. Hence, in this earlier disclosure, the detector can not simultaneously explore a range of wavelengths, which constitutes the basic concept of optical spectroscopy. The earlier disclosure focuses on one wavelength (e.g. NIR wavelength) and measures the corresponding intensity of light received, which is said to be function of the fluid composition to be measured. Furthermore, the teachings of this patent were not intended to detect micro-sized particles, as is the case of the current disclosure.

U.S. Pat. Nos. 5,140,169 and 5,170,056 issued Aug. 14, 1992 and Dec. 8, 1992 respectively. The '169 patent teaches a flow cell while the '056 patent teaches a probe. While both techniques use spectrometry with optical fiber cables, they only handle offline measurements on samples, which are put within a very narrow volume space. Furthermore, the two disclosures do not specify the wavelengths used and consider the light in the transmittance mode only.

Another drawback of the aforementioned prior art is that the disclosures all assume that the continuous phase (i.e. the background surrounding the particles of interest) is constant over time. This constraint is not realistic in oil and gas fields, since the density of the fluid (oil or gas) and even its type is likely to change. For instance, over a period of time, the produced natural gas can change from methane-dominated gas to ethane-dominated gas. Furthermore, when these apparatus operate online, they only monitor a relatively small portion of the flow in a slip-stream sample line either by using measurement cells (e.g. multi-pass measurement cell, cross flow measurement cell, and/or integrating sphere) or immersion probes. Therefore, such methods do not consider the entire process flow and consequently cannot be applied directly to the gas/oil pipelines in order to measure the flow of black powder.

SUMMARY OF THE INVENTION

In a preferred embodiment, the present invention is a non-destructive optical-based device to monitor online and continuously the amount of black powder passing though the earliest stages of the pipeline network. This device will allow isolating highly contaminated pipelines and thus reduce the risks; which may be caused to the pipelines by contamination through the black powder. In one aspect, the device operates using three different techniques (i.e. NIR, MIR, and Raman spectroscopy) to analyze the reflected, transmitted, and refraction light beams, which interact with the target medium. Hence, besides being non-intrusive and non-invasive techniques, the device also employs the property that light in the IR range has a different absorption rate for different constituents of black powder in the target medium. Hence, by knowing the spectrum of each of these different constituents, a proper analysis of the spectrum would lead to a good estimation of the concentration of the different constituents in the target medium.

The device uses an algorithm implemented by a computer program product in a computing device to process the data from the different techniques. In one embodiment two multivariate techniques are used, namely the Principal Component Regression (PCR) and the Partial Least Square Regression (PLSR) techniques. These multivariate techniques are commonly used to group samples with similar characteristics to classify unknown samples (qualitative analysis) or to determine specific properties of unknown samples (quantitative analysis). Other artificial intelligence techniques such as neural network, fuzzy logic or other techniques can also be applied.

In another preferred embodiment of the present invention, the monitors online and continuously the amount of the black powder passing through the earliest stages of a pipeline network. The device allows for reducing of the risks that may be linked to the substantial pressure drops commonly experienced in the downstream pipelines.

In another preferred embodiment, the present invention comprises a ring of optical sender and receiving sensors evenly distributed across a given section of the pipeline. Extensive offline experiments to quantify the amount of black powder were conducted, and the results of the experiments were recorded to create a database of spectra relating to the different concentrations of the constituents of the black powder. The experiments were conducted by first measuring the samples of black powder by standard analytical procedures and then using the results as reference values for establishing the calibration model based on multivariate calibration using the PCR and the PLSR for NIR, MIR, and Raman spectroscopy. The results obtained from these experiments support the feasibility of using optical-based approach to monitor black powder particles in gas pipelines.

In another preferred embodiment, the present invention is an optical-based system and a method for online measurement of sub-micrometer sized black powder in gas or oil pipelines. The system comprises at least one optical light transmitter (also called emitter), which transmits a beam of light towards a target medium within which the black powder concentration is sought to be determined. Depending on the positioning of the transmitters relative to the receivers, the sensing area can be either a two-dimensional (2D) section of the pipeline, or a 3D volume of the target medium. Targeting the 3D volume leads to a better accuracy of measurement at the expense of high computation time and/or hardware complexity. This allows for instance to trigger an early warning for any eventual blockage at some downstream locations of the pipeline network.

A plurality of optical sensors operating within the senders' wavelengths are positioned at different locations in the pipeline to measure the amount of light absorbed and/or reflected by black powder particles. A dedicated pattern recognition algorithm using statistical and/or artificial intelligence approaches uses this data to estimate the amount of black powder passing through the target area. The optical senders and receivers can be connected to the control room via optical fibers, which allow the apparatus to operate safely in hazardous areas (e.g. Zone 0 areas).

Still other aspects, features, and advantages of the present invention are readily apparent from the following detailed description, simply by illustrating a preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description, which follows and in part will be obvious from the description, or may be learned by practice of the invention.

BRIEF DESCRIPTION OF THE DRAWINGS

For a more complete understanding of the present invention and the advantages thereof, reference is now made to the following description and the accompanying drawings, in which:

FIGS. 7A-C show the (A) MIR, (B) NIR, and (B) Raman spectra of black powder used.

FIGS. 11A-C show a PRESS-PLS and PCR for the (A) MIR, (B) NIR, and (B) Raman data.

FIG. 16 shows Table I, which is a summary of the comparison between PLSR and PCR for NIR, MIR, and Raman spectroscopy.

DETAILED DESCRIPTION OF THE PREFERRED EMBODIMENTS

The invention will now be described with reference to the drawings. It will be understood that the embodiments and aspects of the invention described herein are only examples and do not limit the protective scope of the claims in any way. The invention is defined by the claims and their equivalents. It will be understood that a feature of one aspect or embodiment of the invention can be combined with a feature of a different aspect or aspects and/or embodiments of the invention.

Figure 1:
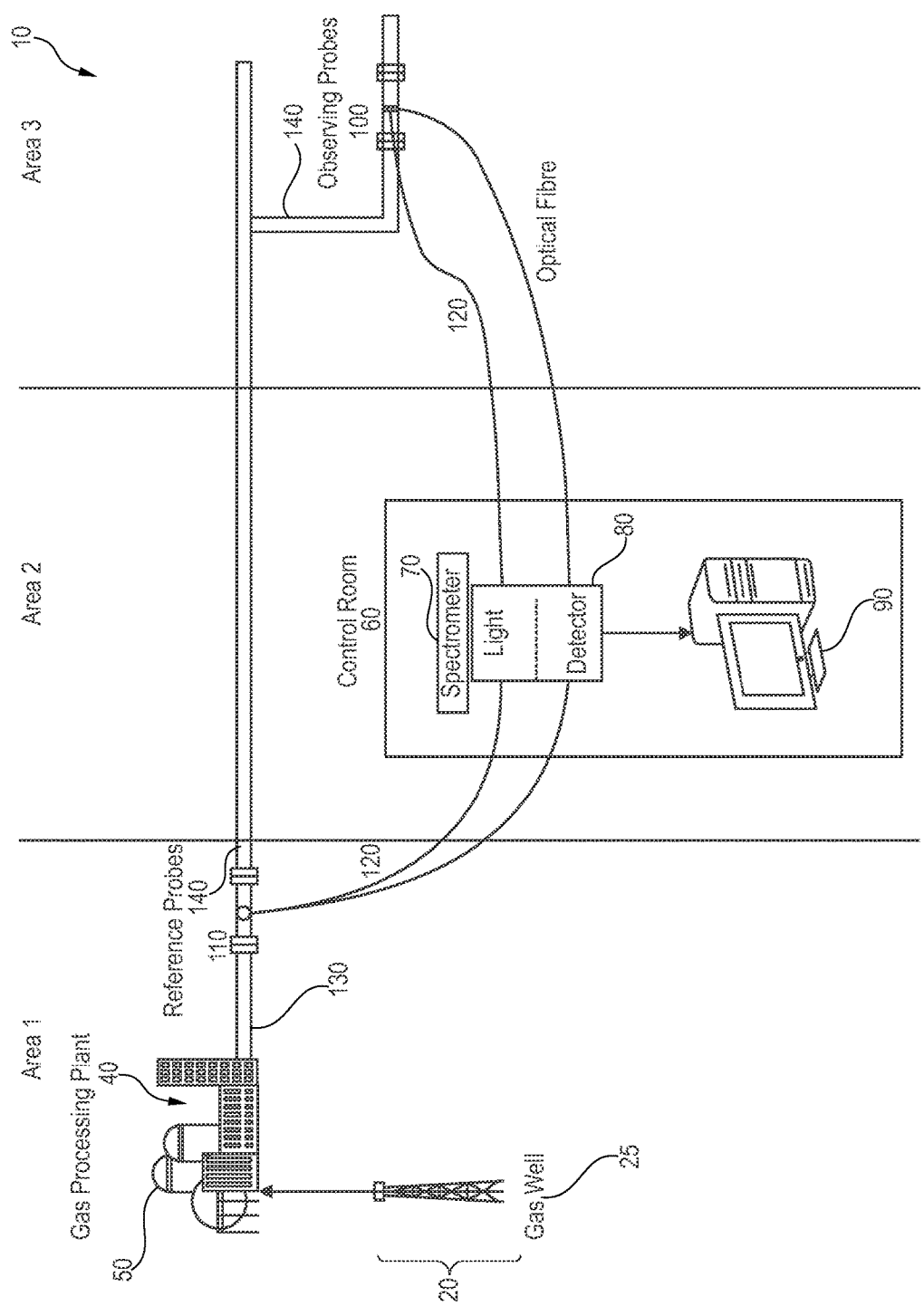
FIG. 1 is a diagram of a preferred embodiment of the present invention in an exemplary system as used in the gas industry.

FIG. 1 shows a global overview of the system 10 in which the device is incorporated and how the system 10 fits into the gas field 20 with one or more gas wells 25. This system 10 comprises three areas: 1) Area 1 comprising an upstream gas processing plant 40 and gas reservoir 50 as well as one or more reference probes 110 in a gas pipeline 130; 2) Area 2 comprising a control room 60 in which all field data are gathered and compiled; and 3) Area 3, comprising a device in accordance with the present invention (i.e., observing probe 100). Without loss of generalities, Areas 1 and 3 can be adjacent and are classified as hazardous areas. Connecting the reference probes 110 in Area 1 and the observing probe 100 in Area 3 to the control room in Area 2 by using optical fibers 120 makes the system 10 safer.

Hence, the system 10 is distributed across all the three areas 1, 2 and 3, which are interconnected via the optical fibers 120. In the control room 60, a spectrometer 70 emits light toward both the reference probes 110 and the observing probes 100 and the emitted light is projected into the gas stream 140 in the gas pipeline 130. The control room 60 is also depicted in FIG. 1 as having a computing device 90. In practice the computing 90 may be located elsewhere and connected to a terminal in the control room 60. The computing device will have logic for performing the calculations set out below, as well as for receiving data and outputting a result.

Only a portion of the emitted light, or photons, will absorbed by the black powder contaminants in the gas stream. The remaining portion of the emitted light is transmitted, reflected, or refracted by the black powder contaminants. The light detector 80 in the control room 60 can analyze the received light from the reference probes 110 and the observing probes 100. The received light will be proportional to the amount of the black powder passing through the gas pipelines 130 and depends on the constituents (contaminants) of the black powder.

In FIG. 1, the reference probe 110 is expected to handle a less complex fluid since the reference probe 110 is placed very close to the gas processing plant 40, which removes various types of impurities from the gas stream 140. Hence, a negligible amount of the black powder is expected to pass through this reference probe 110, while a larger amount of the black powder is gradually generated at the downstream section of the gas pipeline 130, i.e. in Area 3. The role of this reference probe 110 is mainly to identify the type of natural gas passing through the gas pipeline 130. The natural gas in the gas stream 140 is known to have a complex composition of different gases with different concentrations (e.g., methane $CH_4$, ethane $C_2H_6$, propane $C_3H_8$, butane $C_4H_{10}$, hydrogen sulfide, carbon dioxide, water vapor, and sometimes other gases, such as helium and nitrogen—see Liang et al "NIR spectrum analysis of natural gas based on hollow-core photonic bandgap fiber", IEEE Sensors J, vol. 12, no 7, 2362-2367, July 2012). Knowing this complex composition makes the calibration significantly less complex by applying some advanced chemometric techniques that generate a multivariate model, which can distinguish each one of the components in the gas stream 140 and measure its concentration. Hence, by subtracting the wavelength spectrums obtained from the reference probes 110 and the observation probes 100, one can determine the spectrum that corresponds to the black powder in the gas stream 140 at the observation probes 100. This is because the absorption spectra is assumed to be additive in case the substances of the mixture do not interact with each other.

Figure 2:
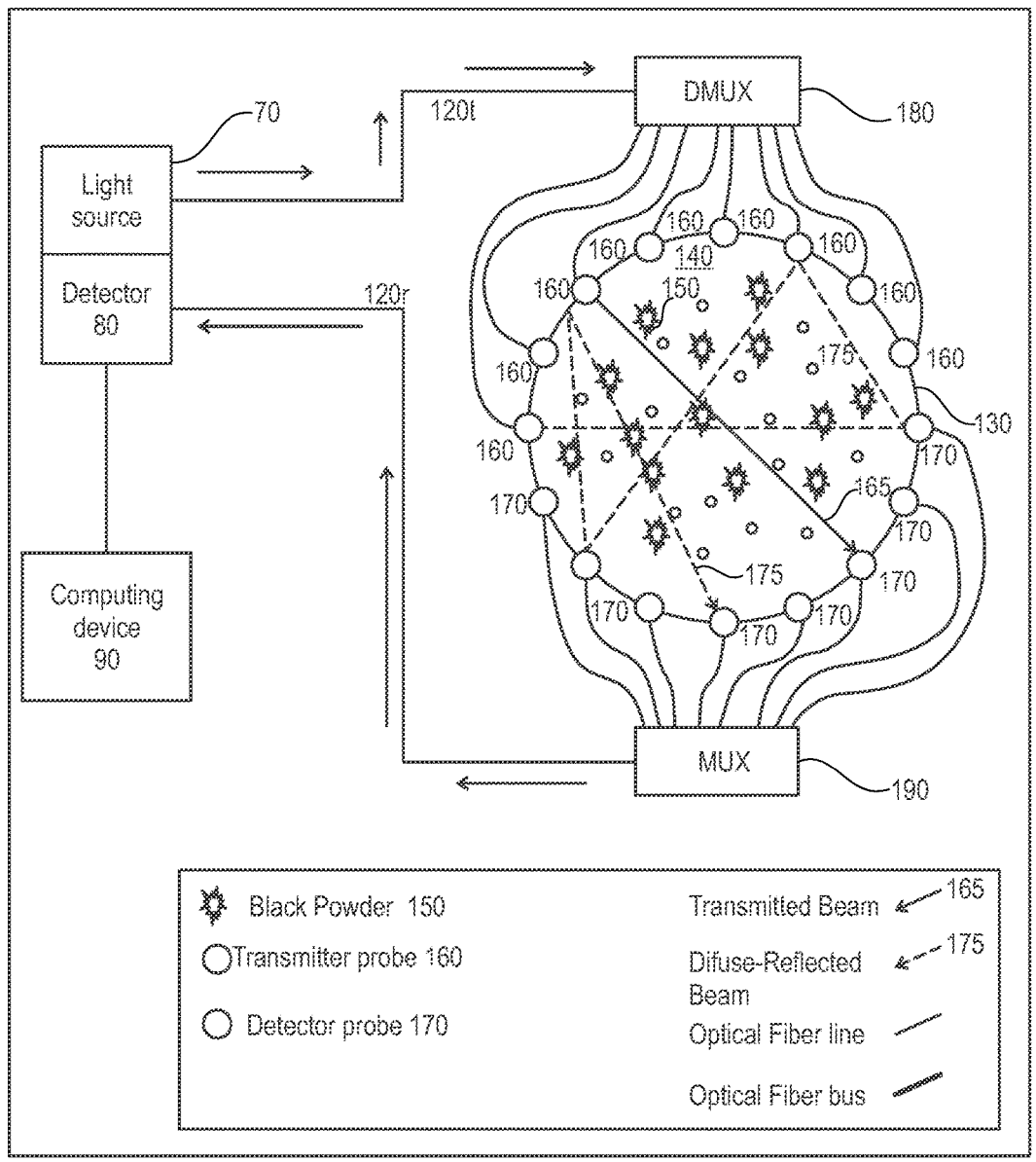
FIG. 2 shows a system in accordance with a first embodiment of the present invention.

FIG. 2 shows a first embodiment of the overall hardware configuration of both the observation probes 100 and the reference probes 110. The hardware configuration comprises a multitude of transmitting optical fibers 120t and receiving optical fibers 120r evenly connected to a same cross section of the gas pipeline 130 via robust transparent adapters (e.g. sapphire windows in the walls of the gas pipeline 130) and remotely connected to a spectrum analyzer device 80. The transmitter probes 160 and the detector probes 170 are connected to the light source 70 through a light demultiplexer 180 and a light multiplexer 190 in order to emit and collect the transmitted, reflected, and refracted light in a time-multiplexed manner. While the light source 70 can emit light, which can be spread over a wide range of wavelengths, the photodetector 80 (also known as light detector) operates within either the NIR or MIR ranges. Hence, the photodetector 80 comprises $2^n$ photo detector elements, where the photo-detector elements are sensitive to a very narrow single wavelength source of light. A transparent prism (not shown) is inserted between the receiving optical fiber 120r and the array of photodetectors elements in the photodetector 80. The computing device 90 reads the values stored by these photodetector elements in a fast serial manner, allowing a real-time data acquisition.

Raman spectroscopy is a technique that is used to monitor the black powder 150 in the gas pipeline 130. Raman spectroscopy is based on inelastic scattering of monochromatic laser light (from the light source 70) by matter. Inelastic scattering is the change of the frequency of photons in the laser light upon interaction with the matter. When the photons of the laser light are absorbed by the matter and then reemitted, the reemitted photons can have a frequency that is shifted up or down when compared with the original laser frequency. This shift is called the Raman effect. This shift offers information about the studied matter by observing the vibrational, rotational, and other low frequency transitions in molecules. A further discussion on the use of the Raman effect to detect solid particles in a fluid is found in Gallego et al, "Rapid measurement of phenolic compounds in red wine using Raman spectroscopy", IEEE Trans. Instrum. Meas. Vol. 60, No. 2, 507-512, February 2011.

In FIG. 2, the device 10 can operate in the transmittance mode, diffuse-reflectance mode or both modes in parallel as will now be explained.

Transmittance Mode

By illuminating one side of the gas pipeline 130, and measuring the intensity of the light that exits from the contaminants of the black powder 150 in an opposite side of the gas pipeline 130, the computing device 90 acting as an analyzer can analyze the relationship between the projected light intensity and the received light intensity to determine the absorption according to Eqn 1:

$$A = \log_1 I_0 / I_1 \quad (1)$$

where A is the absorbance, $I_0$ is the emitted light, and $I_1$ is the detected light.

While the accuracy of the measurement would increase with the increase of the number of the transmitter probes 160 and the detector probes 170, having a homogenous distribution of the black powder 150 in the gas pipeline 130 helps to relax this constraint. Hence, a flow homogenization can be easily obtained by properly designing the gas pipeline 130 preceding the transmitter probes 160 and the detector probes 170 (e.g. by using a T-blender). This approach is commonly considered in flow measurement instrumentation, as noted in Meribout et al "A multisensory intelligent device for real-time multiphase flow metering in oil fields", IEEE Trans. Instrum. Measur., Vol. 59, No. 6, 1507-1519, January 2010.

Diffuse-Reflectance Mode

Diffuse-reflectance spectroscopy is a technique for measuring irregular-shaped materials and powders, especially iron oxides and oxyhydroxides (see Liu et al, "Quantification of hematite from the visible diffuse reflectance spectrum: Effects of aluminum substitution and grain morphology", Clay Minerals, Vol. 46, No. 1, 137-147, 2011. The diffuse-reflectance spectroscopy relies on the principle that when the light beam 165 enters the gas pipeline 130, some of the energy in the light beam is reflected off the surface of the particles in the black powder 150 while some of its energy is transmitted through the particles. The light energy reflecting off the surface of the particle is usually lost while the light energy that passes through the particle is either reflected off the next one of the particles or transmitted through the next particle. This transmission-reflectance event happens many times in the device, which increases the path length of the reflected beam, as discussed in Giusto et al "Monitoring absorption changes in a layered diffusive medium by white-light time-resolved reflectance spectroscopy", IEEE Trans. Instrum. Meas., Vol. 59, No. 7, 1925-1932, June 2010.

When the light beam hits a diffuse surface, the light beam (diffuse-reflected beam 175) creates a "virtual light source" by reflection. Radiance, which is the flux density per unit solid angle, is used to best describe the light energy stemming from the surface. Radiance is used to indicate the amount of flux that is collected by the detector viewing the illuminated surface. The following equation represents the radiance L of a diffuse surface for an input flux, $\varphi_i$.

$$L = \frac{\varphi_i \rho}{\Omega A} \quad (2)$$

where $\rho$ is the reflectance, A is the illuminated area, and $\Omega$ is the total projected solid angle from the surface of the particle.

To derive the radiance L of an internally illuminated reflective loop, the radiance equation (2) must consider the multiple surface reflections as well as the losses through port openings for the transmitter probes 160 and the detector probes. Consider a reflective loop with a transmitter port area $A_t$ and one detector port area $A_e$. When the first beam hits the first spot in the reflective loop, the input flux is perfectly diffused by the first reflection. The quantity of flux incident on the entire reflective loop surface is $$\varphi_{total} = \varphi_i \rho \left( \frac{A_s - A_i - A_e}{A_s} \right) \quad (3)$$

where $A_s$ is the surface area of the entire loop and the quantity in parenthesis represents the fraction of flux received by the loop's surface that is unconsumed by the two port openings, which can be written as $(1-f)$ where f represents the port fraction $(A_t + A_e)/A_s$. Consequently, the total flux incident after n reflections over the entire circle surface is $$\varphi_{total} = \frac{\varphi_i \rho (1-f)}{1 - \rho(1-f)}. \quad (4)$$

Equation 4 shows that the total flux incident $\varphi_{total}$ on the loop surface is greater than the input flux $\varphi_i$ because of the multiple reflections within the circle boundaries. Accordingly, the circle surface radiance is $$L_s = \frac{\varphi_i}{\Omega A_s (1-f)} \times \frac{\rho(1-f)}{1 - \rho(1-f)}. \quad (5)$$
$$= \frac{\varphi_i}{\Omega A_s} \times \frac{\rho}{1 - \rho(1-f)}$$

Equation (5) represents the detected light, which is used in Equation (1) to deduce the absorbance required for the quantitative analysis of the black powder 150. The equation (5) is used to predict the loop radiance for a given input flux $\varphi_i$ as a function of circle diameter, reflectance, and port fraction. Maximum radiance is expected to be detected by the detector probe 170 when there is no black powder 150 in the gas pipeline 130. The radiance fluctuates as the quantity of the black powder 150 fluctuates in the illuminated area A. Accordingly, a quantitative analysis of the black powder 150 can be obtained.

Figure 3:
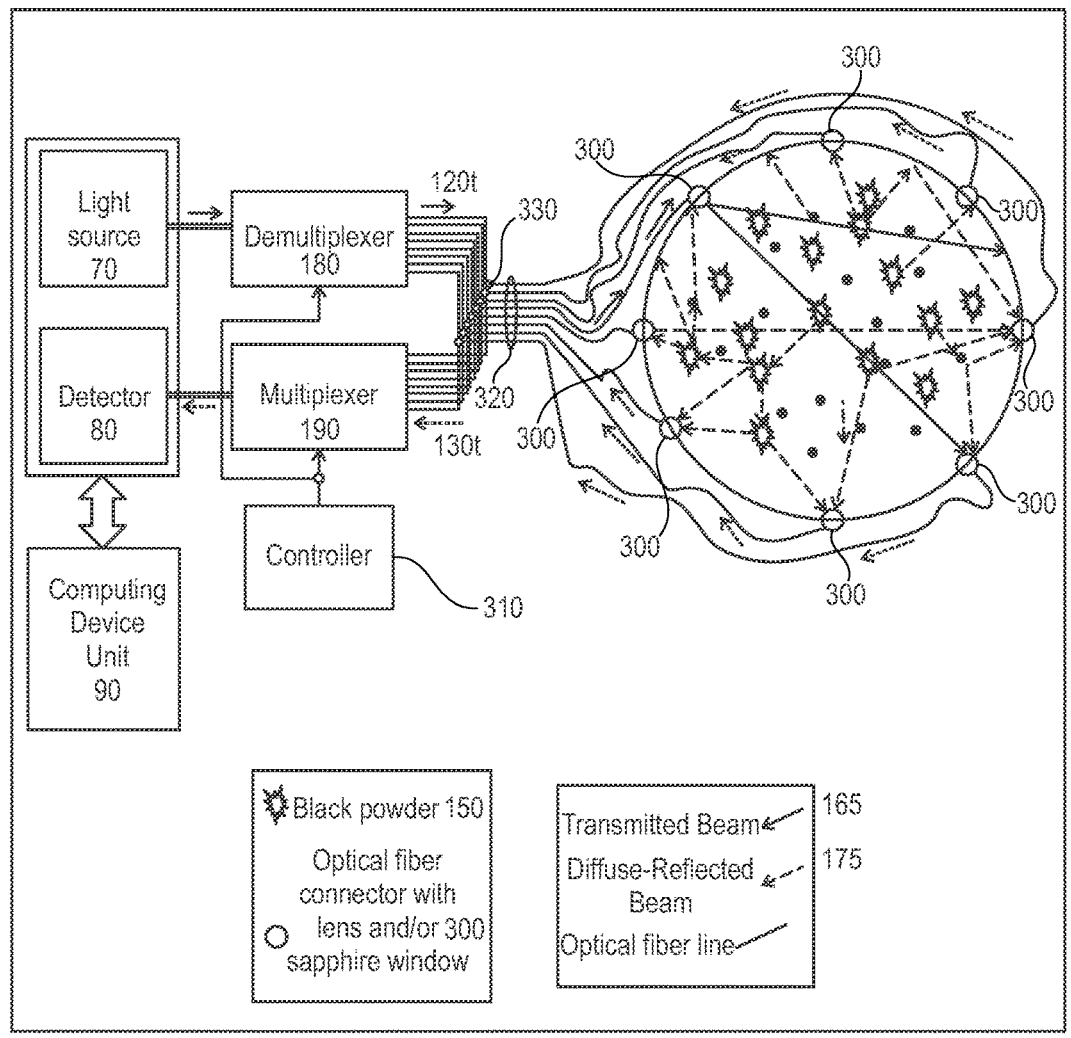
FIG. 3 shows a system in accordance with a second embodiment of the present invention.

FIG. 3 is a second embodiment of the overall detection system where a ring of optical fiber connectors 300 is attached to a plurality of probes with lens and/or sapphire windows in the wall of the gas pipeline 130. It will be appreciated that similar reference numerals are used in FIGS. 2 to 4 to indicate similar elements. Each of these optical fiber connectors 300 receives an amount of light in either direction (transmittance/reflectance), depending on the sequences being executed by a controller 310. The controller 310 is connected to the multiplexer 190 and the demultiplexer 180. The transmitting optical fibers 120t and the receiving optical fibers 120r are connected at a connector 330 to the optical fibers 320 connected to the optical fiber connectors 300.

Figure 4:
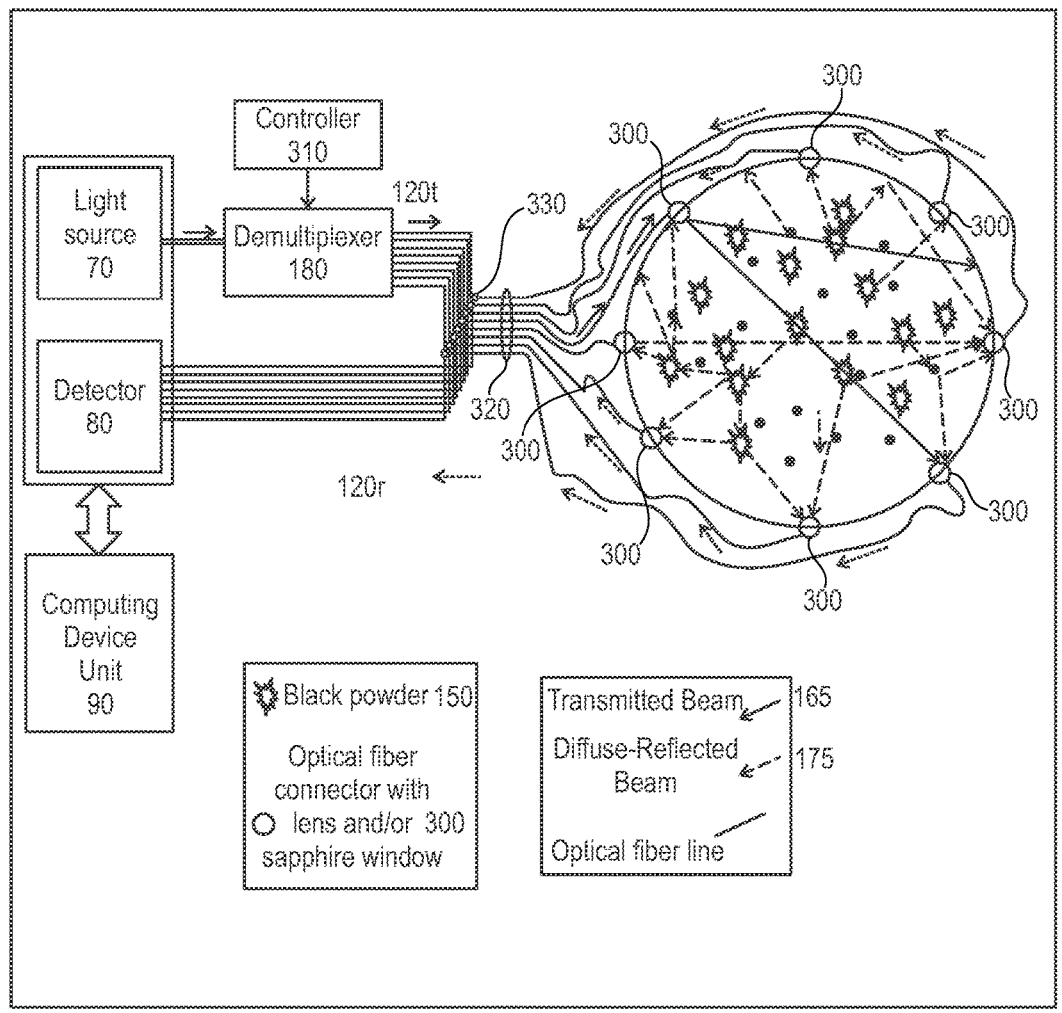
FIG. 4 shows a system in accordance with a third embodiment of the present invention.

FIG. 4 is a third embodiment of the overall system which is similar to the one shown in FIG. 3, except that the receiving light from the receiving optical fibers 120r is simultaneously acquired by a data acquisition module to run a detection algorithm in the computing device 90. This embodiment enables fast detection throughput, but at the expense of higher amount of hardware.

Figure 5:
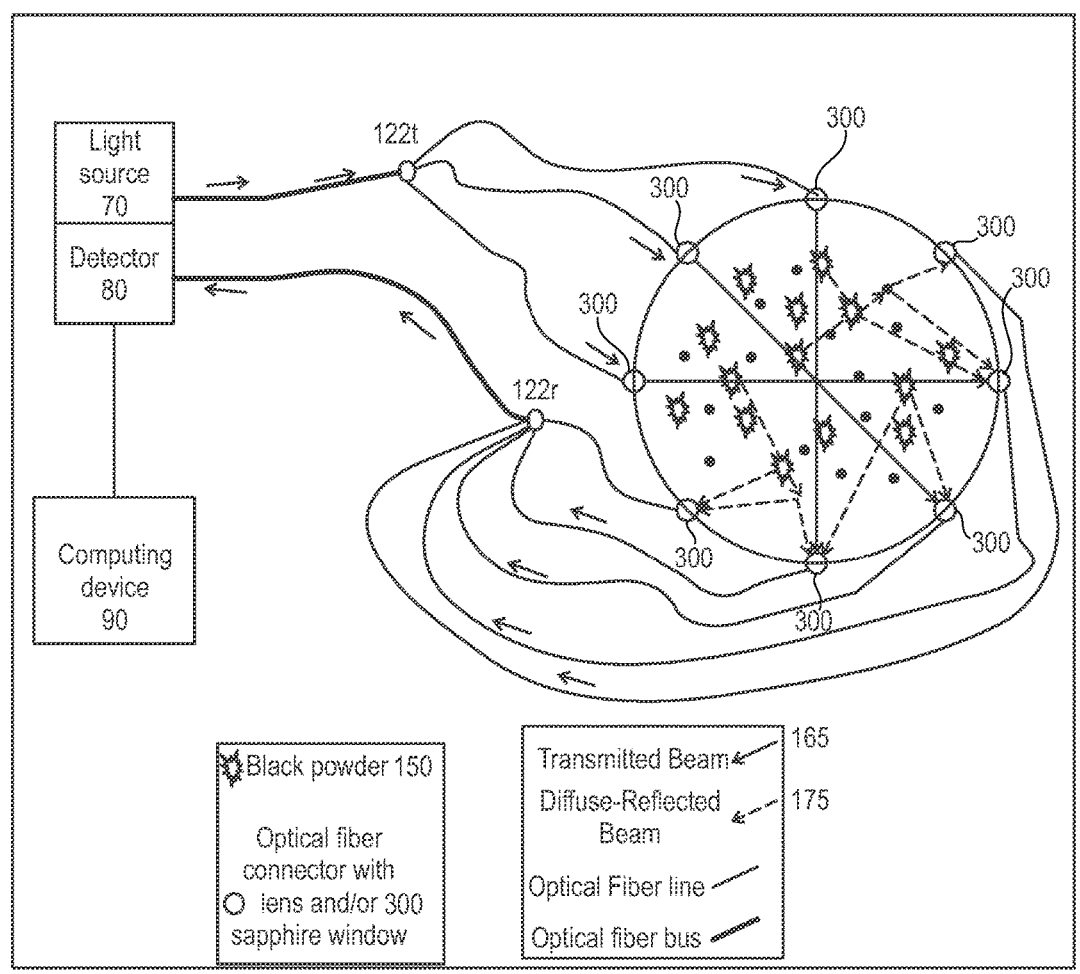
FIG. 5 shows a system in accordance with a fourth embodiment of the present invention.

FIG. 5 is a fourth embodiment of the overall system which is similar to the ones shown in FIGS. 3 and 4 besides the fact that no multiplexer or demultiplexer circuits are used. However, two bundles 122t, 122r of optical fibers which carry a multitude of optical fibers lines in both transmitting modes and receiving modes respectively are used.

Figure 6:
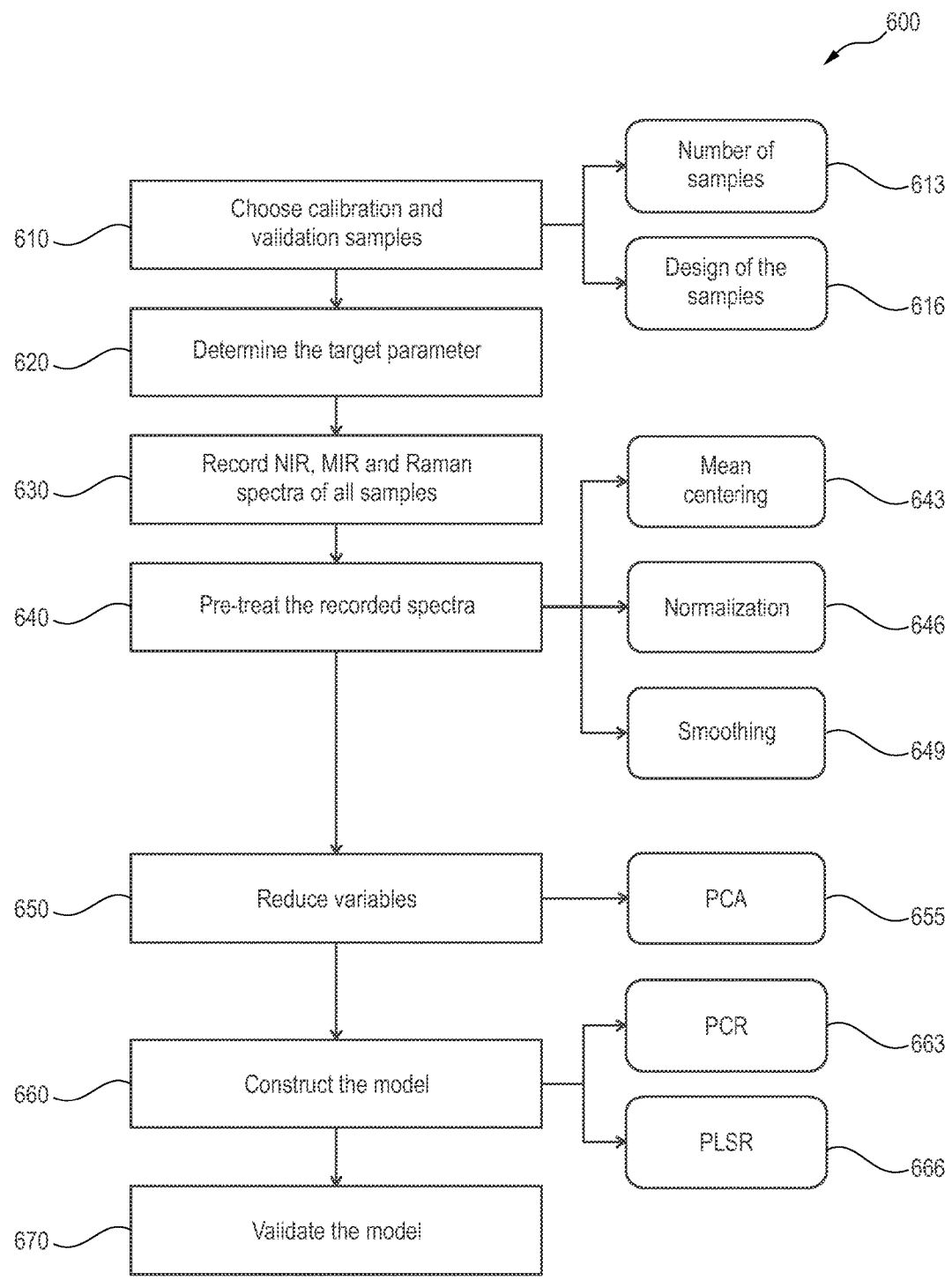
FIG. 6 is a flow chart of multivariate calibration in accordance with a preferred embodiment of the present invention.

FIG. 6 shows the flow chart 600 of the approach carried out to conduct a multivariate calibration model. Details on the steps are given below.

Choosing the Calibration and Validation Samples—step 610.

The number of samples 613 for the calibration and validation should be carefully chosen. Yet, more importantly is considering how to choose them. The calibration samples are also called training set and they are used to conduct the calibration and design the model in step 616. On the other hand, the validation set consists of the validation samples and it is used to validate the model designed and evaluate the calibration performance.

Design of Samples—Step 616

The quality of the calibration depends mostly on the training set used to generate the calibration. The training set must contain all of the unknowns that the calibration should analyze. Since the model to be designed for the calibration is based on statistical techniques, the training set should be a statistically valid sample of the population including all unknown samples for the application. In order to prevent extrapolation, the concentrations of the particles of black powder 130 in the calibration samples should span the full range of concentrations that will exist in the unknown gas stream 140. Since only one component is considered in the experiments, the sample design is not complicated and only requires to vary the concentration of the black powder samples stepwise in order to span the full range of the specified concentrations. However, if more than one component exists in the samples, more attention should be paid for the sample design in step 616.

Determination of the target parameter in step 620.

In order to produce a model that predicts different concentration values of black powder 150 in the gas pipeline 130, target parameters should be determined and the first step is to create a concentration matrix, which will be used later to predict the concentration values. The data set concentration values are used to form the concentration matrix (C). For m components and n samples, the concentration matrix (C) can be assembled as a (n×m) matrix, where the m components in this context mean sources of variation. For simplicity, the black powder 150 was considered as a single one of the m components in the test and ten samples were taken. Accordingly, the concentration matrix (C) was assembled as a (10×1) matrix.

Record NIR Spectra of All Samples—Step 630.

The absorbance matrix (A) represents the spectral data and each spectrum is represented as a column vector. For P wavelengths and n samples, the absorbance matrix (A) can be assembled as an (n×p) matrix. Consequently, for the application of this disclosure, the absorbance matrix for the NIR spectroscopy was assembled as a (10×1400) matrix since the data were taken over P=1400 wavelengths for the ten different samples. On the other hand, the absorbance matrices (A) for the MIR (P=828) and Raman spectroscopy (P=1850) were assembled as (10×828) and (10×1850) matrices, respectively.

The multicomponent form of the Beer-Lambert law is considered the base of quantitative analysis in spectroscopy $$A_i \sum_{i=1, j=1}^{p,m} (\varepsilon_{j,i} b\ c_j) \tag{6}$$

where $A_i$ is the measured absorbance at wavelength i, $\varepsilon_{j,i}$ is the sample's absorptivity of component j at wavelength i, b is the optical path length of the measurement, and $c_j$ is the concentration of component j.

The summation in equation (6) is taken over the m components of each of the samples. However, the term product $\varepsilon_{j,i}$ b, can be combined to produce the sensitivity coefficient $k_{j,i}$, which represents the correlation between the concentration and absorbance. For the m components and the P wavelengths, the sensitivity matrix (K) can be assembled as a (m×P) matrix, which is basically the spectra of each pure component in each raw. After assembling the (A), (C), and (K) matrices, the equation (6) can be defined in matrix notation as.

$$A = CK + E \tag{7}$$

where E represents the error matrix (n×P) which shows that noise, artifact, or other kind of errors cannot be verified by the term C.K and will be presented in the measured absorbance matrix A.

Pretreatment of the Recorded Spectra—Step 640.

Prior to designing a multivariate model for the system 10, data pretreatment techniques are used in step 640 to reduce, remove, or regulate unwanted effects on the spectra caused by physical properties of the samples or instrumental effects, such as light scattering, path length variations, and random noise. Therefore, different ones of the pretreatment methods were applied to the spectra to choose the right ones. It was found that only normalization (step 646) and mean centering (step 643) were chosen to apply to the NIR spectra while the MIR and Raman spectra required smoothing (step 649) in addition to normalization 646 and mean centering 643 as the smoothing 649 helped getting the best results without destroying the information.

Reduction of Variables by Principal Component Analysis—Step 650

Principal component analysis (PCA) is a variable-reduction tool that reduces the dimensions of the original data into less uncorrelated variables comprising only significant information from the sample. The PCA in step 655 uses the directions of maximum variability in sample groupings to generate new axes called principal components (PCs). The new variables (PCs) should have the following criteria.

Comprise of linear combinations of the original variables. The first new axis is in the direction covering most variation.

Every succeeding new variable is orthogonal to preceding variables.

Every succeeding new variable is in the direction covering most of the remaining variation.

The new variables are uncorrelated.

Mathematically, the new variables (PCs) are produced by finding the eigenvectors of the variance matrix of the original variables (wavelengths). Then, use these found eigenvectors as the weight vectors for constructing the variables. The analogous eigenvalues then indicate the amount of the original variance that has been enclosed by each new variable.

The PCA is used for qualitative analysis in which spectra are compared with beforehand known spectra then the difference or the resemblance of those spectra discloses information. If we observe A, we can predict C and K in Eqn 7

$$A = \hat{C}\hat{K} + \hat{E} \qquad (8)$$

where the hat notation (^) used in equation (8) indicates a prediction.

This calculation is done by first performing PCA, which results in an abstract mathematical transformation of the equation (8) and yields the form:

$$A = \hat{C}\vec{K} = \hat{E} = \hat{T} \cdot \hat{P} \qquad (9)$$

where T contains the scores in which the variables are linear combinations of the original variables in A. P is the loadings matrix, which is estimated by regressing A onto T. The residual matrix E is found by subtracting the estimated $\hat{T} \cdot \hat{P}$ from A.

Construct the Model in Step 660.

When the different components of the samples are classified, the next step is to quantitatively identify the concentration of each of the different components. The PCR and PLSR methods permit the prediction of the concentrations for the new samples based on their spectra, as is known from Larrain et al, "A multipurpose portable instrument for determining ripeness in wine grapes using NIR spectroscopy", IEEE Trans. Instrum. Meas., Vol. 57, No. 2, 294-302, February 2008.

Calibration using PCR or PLS can be very simple if we consider only black powder 150 as a single compound and ignore all identities and concentrations of the other compounds.

The PCR in step 663 is performed through four main steps.

Obtain the spectra of the training set to construct the (A) matrix.

Perform PCA on these spectra, and deduce the scores (T) matrix and the loadings (P) matrices.

Determine how many PCs should be retained. For this purpose, leave one out (LOO) cross validation was used.

Perform the regression.

The aim of the calibration in step 663 is to find a relationship between the scores and the true concentrations of each compound in the gas stream 40, which takes the form $$c = T \cdot r \qquad (10)$$

where c is the known concentrations in the mixture spectra in the gas stream 140, and r is a column vector, which represents the estimated regression coefficient whose length equals the number of PCs. r can be estimated by the known c and (T) (obtained from PCA) as $$\hat{r} = T^+ \cdot c. \qquad (11)$$

This allows the PCR approximation of the concentration C(CPR) vector to be computed $$c_{(PCR)} = T \cdot T^+ \cdot c. \qquad (12)$$

$T^+$ is the pseudo inverse of T. If there are numerous compounds of interest, the vector c can be expanded to a matrix (C), in which each column corresponds to a compound $$C = T \cdot R. \qquad (13)$$

In order to estimate the quality of prediction, the equation (12) is applied to the test or validation set before estimating real data of unknowns.

The PLSR components in step 666 are acquired using both (A) and c data simultaneously, which maximize the covariance between them. The covariance in PLSR is modeled by finding a variable that maximizes the product of the experimental data with the concentrations. Basically, the PLSR assumes that errors exist in both blocks, which are equally important as opposed to PCR which assumes that all the errors are in the measured data. The PLSR is presented by $$A = T \cdot P + E$$

$$c = T \cdot q + f \qquad (14)$$

where the first equation in (14) appears similar to that of PCA except that the scores matrix (T) models both the concentrations and the spectra. The vector q in equation (14) has some analogy to a loadings vector and it is estimated by regressing c onto T. f is the error vector for the c block and it is calculated by subtracting the estimated T·q from c. After defining the new scores and loadings matrices and vectors the regression is done the same way as PCR.

Validate the Model Using Cross Validation—Step 670.

The optimal number of PCs is determined by cross validation. The LOO cross validation is used in this disclosure. This is done by removing one sample from the calibration set, using the remaining for calculating a new calibration, and using the new calibration to predict the concentrations of the removed sample. Each prediction is then compared with the actual concentration, which is already known, as the removed sample is part of the total calibration set. This procedure is repeated N times (where N is the number of samples in the calibration set), each time leaving out one sample and performing the calibration on it until all samples are tested. This is done in order to determine the best number of PCs (or factors) by trying all numbers of factors.

Both the PCR and the PLSR models for NIR, MIR, and Raman spectroscopy were evaluated to determine their efficiency. The following criteria were calculated and compared.

Predicted Residual Sums of Squares

The size of the errors in the models can determine their quality. Therefore, the sum of squares of E (in PCR and PLS) and f (in PLS) is calculated which measures the accuracy of the prediction by taking the sum over all squared differences between cross validation predicted and true known qualities for all N samples $$PRESS = \sum_{i=1}^{n} (c_{predicted,i} - c_{known,i})^2. \quad (15)$$

Also, the number of significant PLS and PCR components are estimated according to the size of these errors using cross validation, the smaller the error is, the better the model.

Coefficient of Determination $R^2$

The coefficient of determination $R^2$ provides a measure of how well future outcomes are likely to be predicted by the model. It is represented by the total sum of squares divided by the residual sum of squares all subtracted from 1

$$R^2 = 1 - \frac{SS_{err}}{SS_{tot}} \quad (16)$$

where $$SS_{err} = \sum_i (y_i - f_i)^2 \quad (17)$$

$$SS_{tot} = \sum_i (y_i - \bar{y})^2 \quad (18)$$

$y_i$ is the observed value, $f_i$ is the predicted value, and $\bar{y}$ is the mean of the observed data.

Ideally, a perfect model has $R^2=1$, however, in practice a high value of $R^2$ almost equal to one is enough to represent a good model.

For a process device, the computation time is a factor in order to rapidly monitor the continuous process. The less required computation time of the designed model, the faster the analysis is done. The computation time takes into account the preprocessing task, as well as the PCR or PLSR timing requirements. For the offline experiment, the computation time required for running the MATLAB code for the preprocessing task and the PCR/PLSR was calculated using built in special MATLAB codes.

In the real device, the preprocessing task, such as the smoothing operation (step 649), features local computation requirements, which can be effectively implemented on a VLSI device, such as field programmable gate array (FPGA). Hence, a first in first out memory device is fed to the smoothing circuit to provide the input noisy spectrum. In this way, the filtered spectrum is generated on the fly with no delay. The number of logic blocks used within the FPGA device is proportional to the window size of the filter being considered. Hence, for a typical window size of eight (8), seven (7) logic blocks are required. This constitutes a negligible hardware requirement with regard to the capacity of modern FPGA devices, which contain hundreds of thousands of logic blocks. The remaining resources can be used for the post processing tasks.

The mean squared error of prediction (MSEP) is often used to assess the performance of regressions. Furthermore, the MSEP is used for selecting the optimal number of components in (PCR) and (PLSR). In order to perform the MSPE, the training data set $(L)=\{x_i,y_i\}$ of $n_L$ observations is randomly divided into K segments $L_k$, where $k=1 \ldots$ to $\ldots$ K, of approximately equal size. The equation (19) represents the MSPE where $f_k$ is the predictor (PLSR and PCR) trained on $L/L_k$, i.e., all observations not in $L_k$. The K-fold cross validation estimate is $$MESP_{cv,K} = \frac{1}{nL} \sum_{k=1}^{K} \sum_{i \in L_k} (f_k(x_i) - y_i), \quad (19)$$

where the inner sum is taken over the observations in the kth segment. The LOO cross validation is the K-fold cross validation with. $K=n_L$

EXAMPLES

Materials: The black powder samples were obtained from ASAB field, GASCO, Abu Dhabi, United Arab Emirates.

Instrumentation. A UV-vis-NIR Carry 5000 spectrophotometer was used for the NIR measurements. The measuring method was transmittance and the NIR spectra were obtained as absorbance in the 800-2200 nm range with a resolution of 1 nm.

The FT-MIR transmission spectra were recorded on a Vertext-70 from Bruker FT-MIR spectrometer (Appendix E) to obtain the MIR spectra. The spectra were recorded at 4 $cm^{-1}$ resolution in the 525-3897 $cm^{-1}$ spectral range.

Raman spectra were obtained using LabRam HR spectrometer, manufactured by Horiba Scientific. The He—Ne laser operates at 633 nm with a maximum power of 2 W and a focal length of 50 mm. A laser output power of 1.2 W was used, which was low enough to prevent possible laser induced sample damage and a high signal to noise ratio. Data were collected at 1 $cm^{-1}$ resolution. Spectra were used in the Raman shift range between 150 and 2000 $cm^{-1}$.

All of the black powder samples were stored and their spectra were obtained at 25° C. room temperature. The spectral range specified for each measurement was determined by the spectrometers used.

Sample Preparation and Recording of Spectra

For the NIR spectra, ten samples of the black powder 150 ranging from 200 to 2000 ppm were prepared. The black powder 150 was mixed with distilled water in an ultrasonic-based mixer for 30 min to suspend the black powder particles 150 in order to mimic its suspension in the gas process. After mixing, the black powder 150 was quickly transferred to a cuvette to take the measurement while the particles of the black powder 150 are still suspended in the liquid. Another cuvette containing distilled water was used as a reference.

In another set of experiments, ten spectra were acquired using MIR and Raman spectroscopy directly without any sample preparation. Samples with different dry black powder contents were prepared by varying the depth or thickness of the black powder layer facing the MIR/Raman light source. The depth of powder was 2-10 mm.

Data Processing

All data processing was coded in MATLAB programming language, Version 7.0.1 (the Math Works, Natick, Mass., USA).

Spectral Features

FIG. 7 shows all the ten (10) MIR (FIG. 7A), NIR (FIG. 7B), and Raman spectra (FIG. 7C) of the black powder samples used in this disclosure. These spectra provide information of all the components of the black powder 150. The absorption bands in the spectra represent the chemical groups of components present in the samples. Although the NIR spectra (FIG. 7B) show clearer and simpler spectral differences among the samples, the MIR and Raman spectra FIGS. 7A and 7C have more information and sharper peaks. Overall, the MIR spectra (FIG. 7B) offer greater spectral features and resolution, yet the MIR spectra in FIG. 7B comprise more spectral noise and baseline variation. Also, it is evident from FIG. 7A that the black powder 150 has very low absorption in the MIR range. On the other hand, the band in the NIR (FIG. 7B) is wide and less sensitive compared with the MIR spectra in FIG. 7A and the Raman spectra in FIG. 7B.

PLSR and PCR Calibration Models for NIR, MIR, and Raman Spectroscopy

Figure 8:
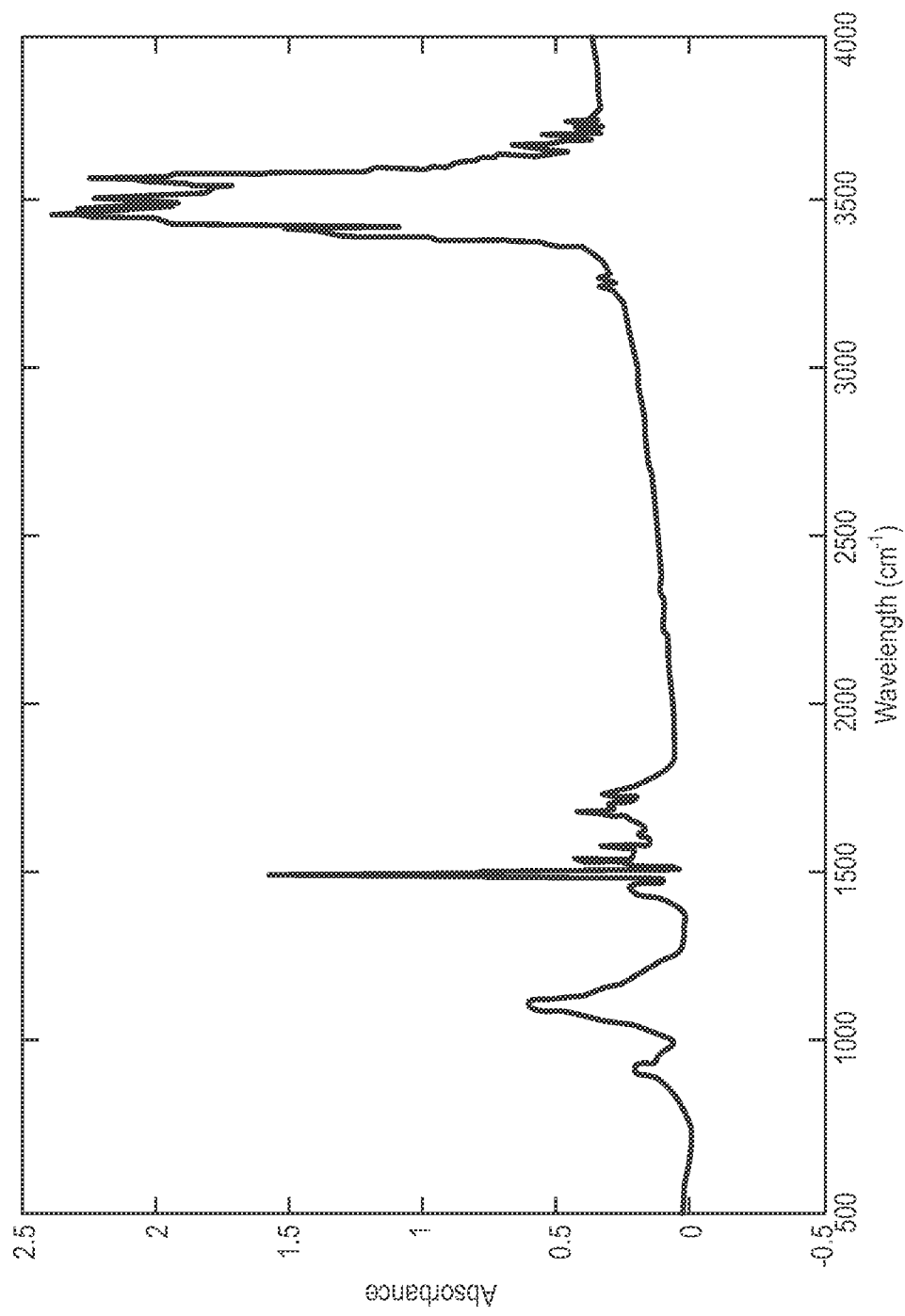
FIG. 8 shows an MIR spectrum of black powder mixed with sand, methane, and ethane gas.
Figure 9:
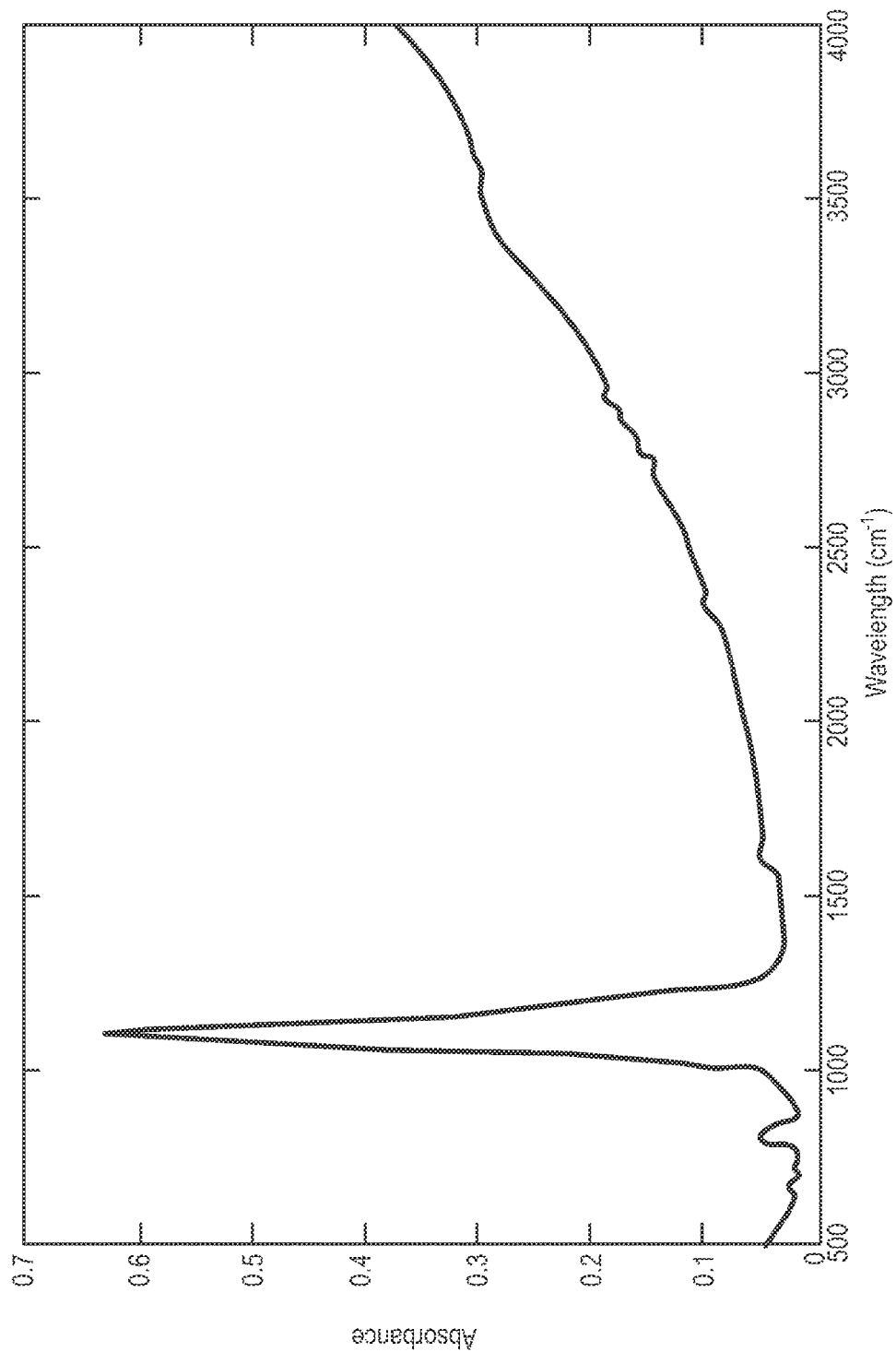
FIG. 9 shows an MIR spectra of black powder mixed with sand after extracting methane and ethane gases.

In order to simplify the calibration process, the pure natural gas spectrum should be extracted from the acquired online spectrum before analyzing the data. In an attempt to mimic the black powder 150 in real natural gas pipelines 130, which contain many different contaminants, sand, methane gas, and ethane gas spectra were added to the black powder spectra. FIG. 8 shows the resultant MIR spectrum of black powder mixed with sand, methane, and ethane gas before extraction. FIG. 9 shows the MIR spectra of black powder mixed with sand after extracting methane and ethane gases.

Figure 10:
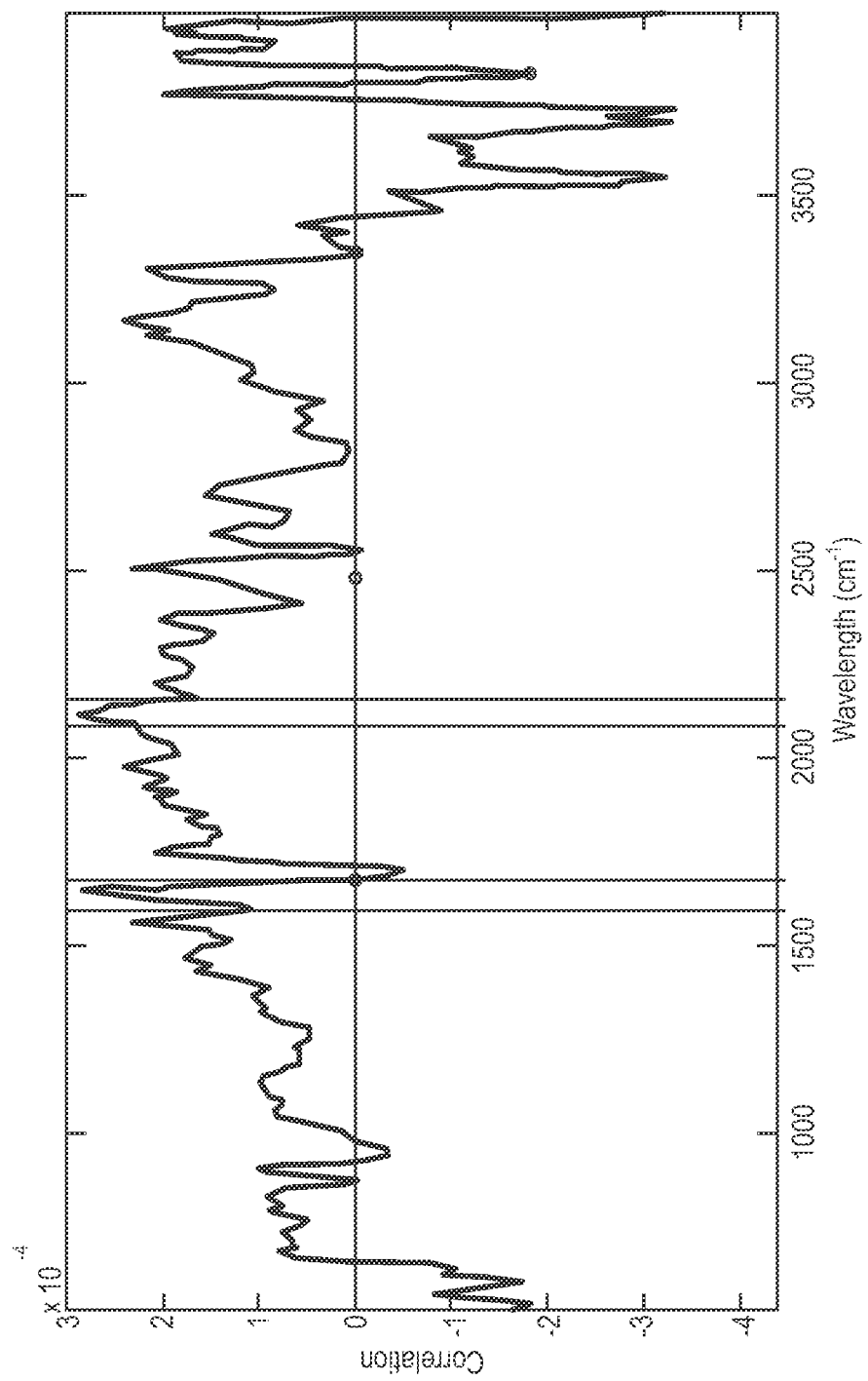
FIG. 10 shows a correlation spectrum for black powder.

In both the PLSR and PCR calibration models, the spectral range and number of PLSR factors are critical parameters and the calibration performance depends on them. Therefore, only the regions (1300-3000 cm$^{-1}$) of the MIR, (1300-1900 nm) of NIR and (200-1400 cm$^{-1}$) of the Raman spectra were considered as these ranges contain most of the useful information. Decreasing the calibration regions also helped in increasing the speed of the analysis and thus save computational time. This spectral range is further reduced and only critical ranges, which include information about the black powder should be considered to avoid the effect of sand. The chosen spectral range must include information describing the concentration variation of the black powder while excluding regions conquered by noise or other constituents. The proper spectral ranges can be recognized by calculating the correlation spectrum for each constituent of interest (FIG. 10), i.e., different spectral ranges can also be used to identify the quantity of sand. This is done by calculating the correlation of the absorbance at every wavelength in the training set spectra to the concentrations of black powder. Only high correlation regions should be selected and low or no correlation regions should be ignored. FIG. 10 shows high correlation bands at (1614-1661) and (2099-2145) cm$^{-1}$ for the black powder 150. These regions are selected for PLSR and PCR calibrations to determine the concentration of black powder since they are mostly conquered by characteristic absorptions due to the black powder only.

The optimal number of components for PCR and PLSR is determined before the predictions of new samples; it is a part of the calibration. The optimal number of factors is the number that results in the best prediction; hence, the optimum number of factors was identified as the number of factors that result in minimum predicted residual sums of squares (PRESS). The evaluation of the calibration and prediction performances is estimated by calculating the coefficient of determination R$^2$ and the MSPE values. Prior to calibration, the NIR, MIR, and Raman spectra were mean centered (step 343) and normalized (step 646) while only the MIR and Raman spectra were smoothed (step 649).

In order to test PCR and later PLSR, a random selection of three validation samples from the total data set were removed. The remaining seven spectra and their known concentrations serve as the calibration set that is used then to predict the unknown concentrations of the validation set. The predicted concentrations are then compared with their known concentrations.

FIG. 11 shows a plot of the PRESS function, which performs the systematic cross validation for up to six principal components. The optimum number of principal components (or factors) for the NIR and Raman PCR calibration model is 2, which present a PRESS of 0.005344 and 0.0002402, respectively. The minimum value for the MIR PCR model is clearly associated with three factors with a PRESS value of 0.00202; however, this value does not significantly differ from the two factors (0.002126), which also can be used to obtain good results. On the other hand, the PLSR calibration model in FIG. 11 shows that the optimum number of components for NIR, MIR, and Raman is 2 with a PRESS value of 0.005467, 0.002099, and 0.0002329, respectively.

Figure 12A:
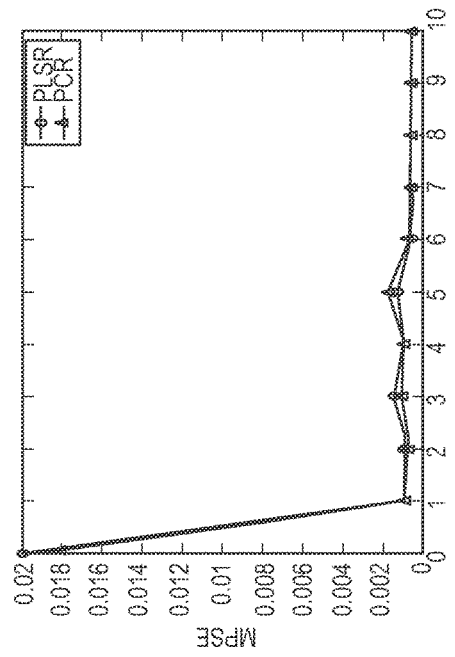
FIGS. 12A-C show MSPE curves for the PLS and PCR for (A) MIR, (B) NIR, and (C) Raman data set.
Figure 12B:
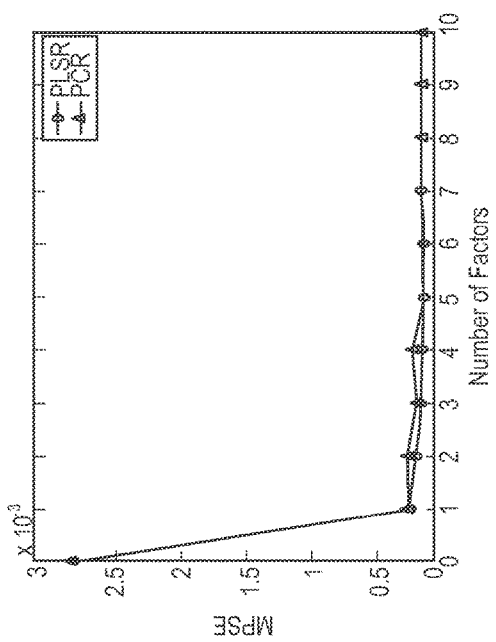
Figure 12C:
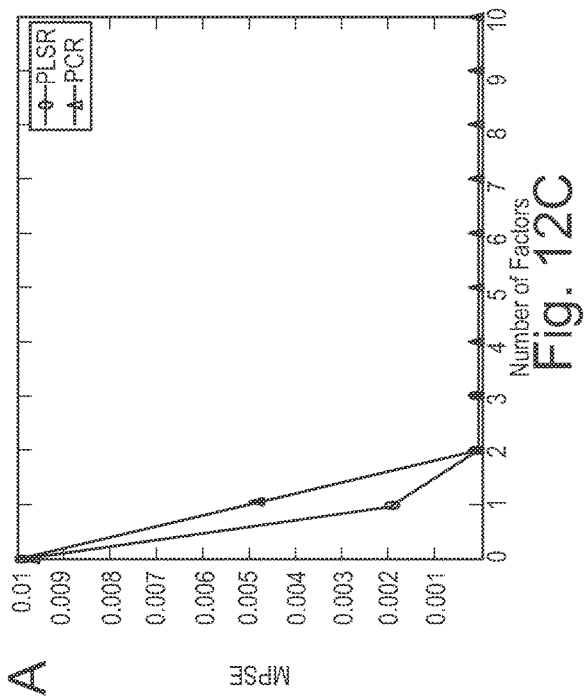

The MSPE for the PLSR is 0.0008731, 0.0001983, and 5.04e-5 for NIR, MIR, and Raman, respectively; while for the PCR it is 0.0009065, 0.0002068, and 5.099e-5, see FIG. 12. It is expected that the MSPE decreases sharply with the initial factors and continues to decrease as more related spectral variation is assimilated into the calibration model. As the number of factors increases further, the MSPE begins to increase indicating that the data has been over-fit by including spectral information into the model that is not related to the concentrations property.

Figure 13A:
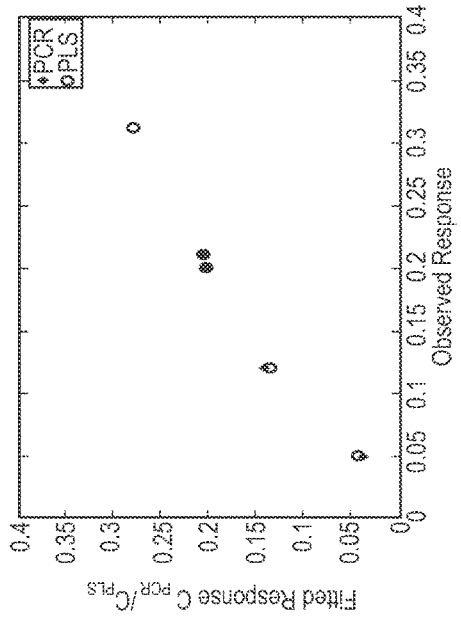
FIGS. 13A-C show PCR and PLS calibration of the (A) MIR, (B) NIR, and (B) Raman data set.
Figure 13B:
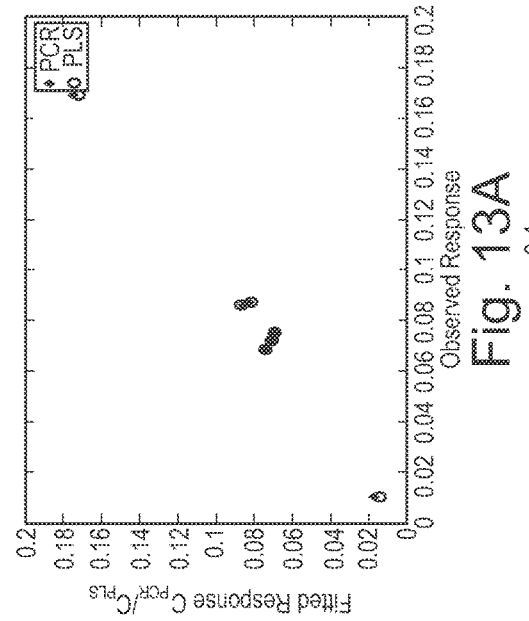
Figure 13C:
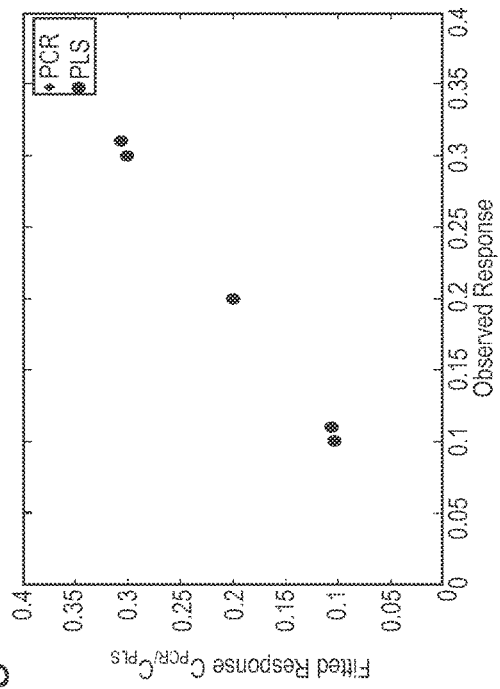

FIG. 13A shows the PCR and PLSR calibration for the MIR using only two factors for the PLSR model and three factors for the PCR model. FIGS. 13B and 13C show the PCR and PLSR calibration for the NIR and Raman models, respectively, in which both PLSR and PCR used two factors.

Figure 14A:
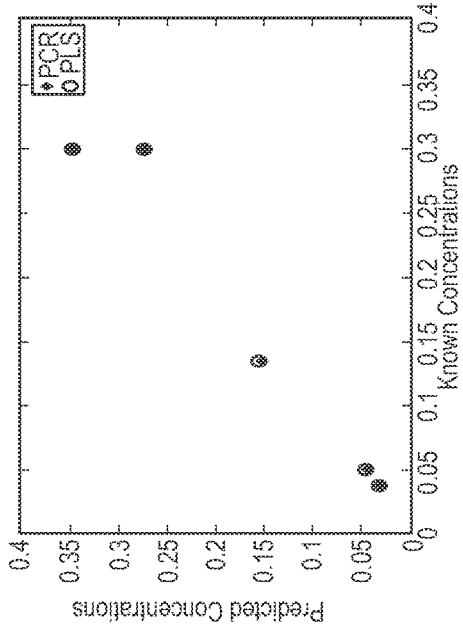
FIGS. 14A-C show PCR and PLSR prediction of three new samples for (A) MIR, (B) NIR, and (C) Raman calibration models.
Figure 14B:
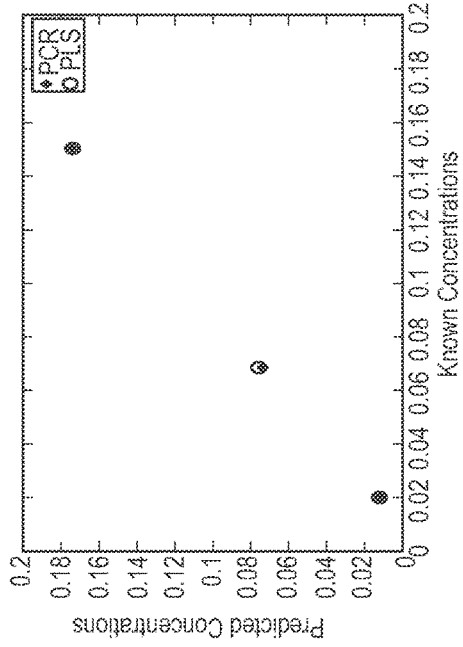
Figure 14C:
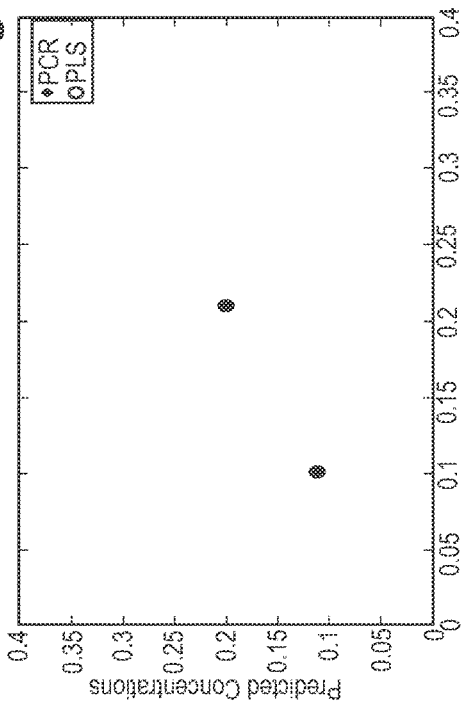

Furthermore, in order to validate the model, the prediction of the three validation samples is performed and shown in FIG. 14. As it is expected already from the high R$^2$ (FIG. 16) and the low MSPE values, all three techniques show very high precision and accuracy.

Figure 15A:
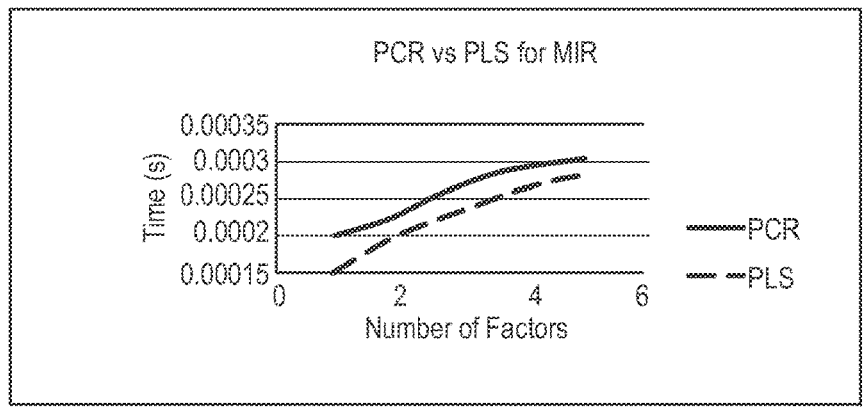
FIGS. 15A-C show computation time for the prediction analysis for (A) MIR, (B) NIR, and (B) Raman models.
Figure 15B:
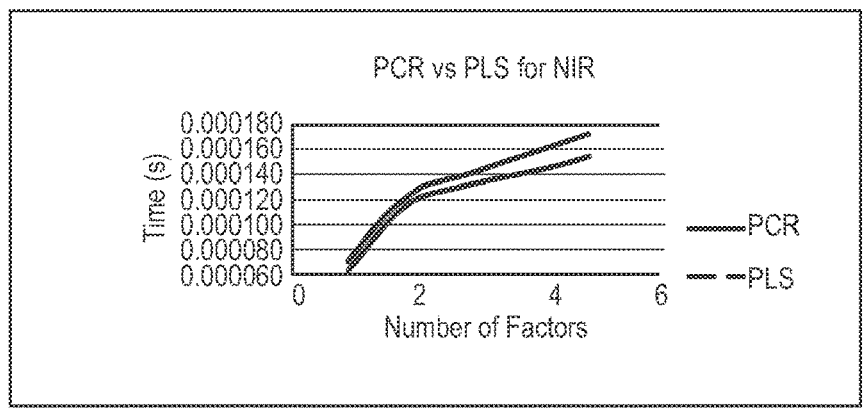
Figure 15C:
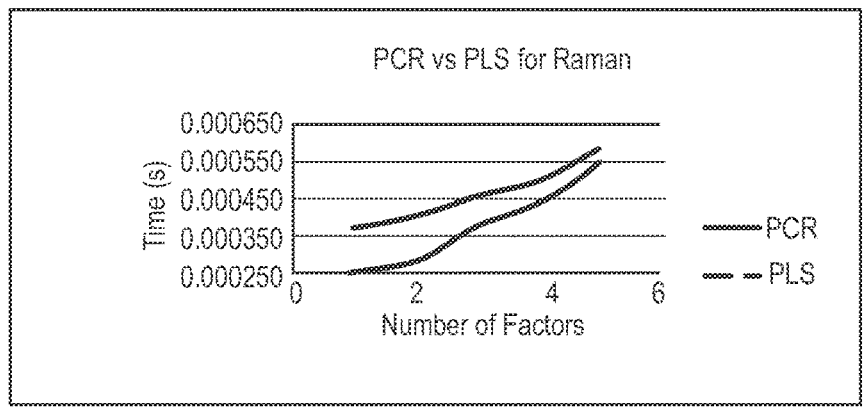

This disclosure discusses different IR spectroscopic techniques for gas monitoring in the pipelines and the computation time for the prediction analysis is a factor. The computation time for all three techniques as a function of PLSR and PCR factors is shown in FIG. 15. Although increasing the number of PLSR and PCR factors result in better prediction (only to a certain number and then the data get over-fitted), it also increases the computation time required.

Comparing PLSR and PCR Methods

FIG. 16 summarizes the comparison between PLSR and PCR for all three techniques. Since these models adapt only ten samples, it is expected to have a smaller scale for all statistical results and comparison; hence, it is noticeable that two PLSR and PCR factors is enough to perform an excellent calibration although it is also possible to get good results with one factor. The correlations R$^2$ between the predicted and actual values for the black powder 150 were very high for both PLSR and PCR methods. The accuracy of the above models was considered sufficient since testing was done with samples that cover a broad range of concentrations.

In view of the similarity of the PRESS results for PCR and PLSR, it is anticipated that the predicted concentrations are very similar for the three methods. Comparing the R$^2$ and MSPE values for the PLSR and PCR, it can be concluded that both methods are almost indistinguishable in their outcome. However, PLSR seems to reach optimal prediction with fewer factors than PCR. Also, PLSR seems to be accomplishing the prediction analysis faster than PCR (FIG. 15), which serves as an advantage for online monitoring especially when a plurality of the transmitter probes 160 and the detector probes 170 are used for the monitoring. In addition, in an attempt to check the robustness of both methods, the true concentrations were varied and the prediction capabilities of both methods were observed. As expected, the PLSR method gave a better prediction than PCR since PLSR components are acquired using both the spectra and the concentrations data simultaneously which maximize the covariance between the two data sets, unlike PCR which only considers the spectra data when calculating its factors. Hence, the PLSR is more robust and can compensate for systematic and human errors more than PCR.

Comparing NIR, MIR, and Raman Techniques

As shown in FIG. 16 all three techniques can be used to obtain an excellent calibration model. However, in account of the calibration and prediction performances, the Raman technique shows slightly better results than NIR and MIR techniques considering the $R^2$ and MSPE values. However, the Raman spectroscopy requires the use of powerful lasers as the sources of light 70 and their optical alignment in order to create an intense and focused path of radiation on the sample, and usually only a professional operator with adequate skills can acquire the proper alignment. Hence, for rapid online monitoring, more experiments should be conducted for Raman spectroscopy before obtaining any conclusive decision on its efficiency.

On the other hand, the MIR spectra are the richest in information among all three techniques, as evident from FIG. 7A. Therefore, the use of MIR spectra is good for multicomponent quantitative analysis where several constituents are to be identified and measured. However, the MIR spectroscopy technique does not have an established multiplexing capabilities nor does the MIR spectroscopy technique support long optical fiber cables. These two criteria are crucial for the requirement of this paper and the proposed device in order to be able to monitor black powder in remote hazardous pipeline systems.

Although NIR is poor with obvious information content, sophisticated chemometric methods, such as PLSR and PCR can be applied to its spectra to extract useful information and perform quantitative analysis. In addition, its ability for online monitoring via optical fibers and its multiplexing capabilities make NIR spectroscopy preferable to MIR spectroscopy despite the slightly better results of MIR shown in FIG. 16. Again, these models considered only ten samples, which resulted in a very small scale for all statistical results; hence, if a conclusion can be drawn, it is that the Raman technique with the use of PLSR regression appears to have the potential for calibrating a better system only for the offline experiment conducted for this paper. Yet, MIR and NIR techniques produced good prediction results as well and can be alternatively considered with the expectation of good results. Therefore, since all techniques produced good models, a feasibility study can be conducted in order to determine the best option for real-time remote online monitoring.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method for determination of contaminants in a flowing fluid within a main pipeline comprising:

Transmitting, via a plurality of transmitters circumferentially arranged on a wall of the main pipeline online of a main flow path of the main pipeline, a plurality of light beams with a spectrum of wavelengths through the flowing fluid in the main pipeline;

receiving a plurality of measurements, via a plurality of receivers circumferentially arranged on a wall of the pipeline online of the main flow path of the pipeline substantially opposite of the transmitters, relating to scattering of the transmitted light beams with the spectrum of wavelengths;

comparing the received plurality of measurements with a plurality of stored patterns; and outputting a result indicative of a determination of contaminants in the fluid flowing in the pipeline.

2. The method of claim 1, wherein the received plurality of measurements relate to at least one of NIR, MIR or Raman spectra.

3. The method of claim 1, further comprising a step of pre-processing the received plurality of measurement prior to the comparing with the plurality of stored patterns.

4. The method of claim 1, further comprising reducing the number of the received plurality of measurements prior to the comparing with the plurality of stored patterns.

5. The method of claim 1, wherein the comparing is carried out by at least one of principal component regression or partial least squares regression.

6. The method of claim 1, wherein the contaminants are solid particles.

7. The method of claim 1, wherein the contaminants are black powder.

8. The method of claim 1, wherein the flowing fluid is gas.

9. The method of claim 1, further comprising a step of establishing a background value for contaminants in the flowing fluid and subtracting the background value prior to the comparing of the received plurality of measurements with the plurality of stored patterns.

10. A system for the determination in a main pipeline of contaminants in a flowing fluid in the main pipeline comprising:

a plurality of transmitters coupled to the pipeline configured to transmit a plurality of light beams with a spectrum of wavelengths through fluid flowing online with the main flow path of the main pipeline;

a plurality of receivers coupled to the main pipeline configured to receive a plurality of measurements relating to transmitted and scattered light beams with the spectrum of wavelengths; and a computing device configured to compare the received plurality of measurements with a plurality of stored patterns and outputting a result indicative of the determination of contaminants in the fluid flowing in the pipeline;

wherein the at least one of the transmitters is arranged on a wall of the pipeline substantially opposite one of the receivers on the wall of the pipeline and wherein the plurality of transmitters and the plurality of receivers are arranged circumferentially about the main pipeline online with the main flow path of the main pipeline.

11. The system of claim 10, further comprising a reference probe in the pipeline for establishing a background level of a contaminant.

12. The system of claim 11, wherein the reference probe is located substantially near a gas processing plant.

13. The system of claim 10, wherein the contaminants are solid particles.

14. The system of claim 10, wherein the contaminants are black powder.

* * * * *